United States Patent
Wang et al.

(10) Patent No.: US 12,059,290 B2
(45) Date of Patent: Aug. 13, 2024

(54) FETAL HEAD DIRECTION MEASURING DEVICE AND METHOD

(71) Applicant: GUANGZHOU LIAN-MED TECHNOLOGY CO., LTD., Guangdong (CN)

(72) Inventors: Youping Wang, Guangdong (CN); Xiaoxing Lu, Guangdong (CN); Kai Wang, Guangdong (CN)

(73) Assignee: GUANGZHOU LIAN-MED TECHNOLOGY CO., LTD., Guangdong (CN)

( * ) Notice: Subject to any disclaimer, the term of this patent is extended or adjusted under 35 U.S.C. 154(b) by 139 days.

(21) Appl. No.: 17/409,444

(22) Filed: Aug. 23, 2021

(65) Prior Publication Data
US 2022/0039774 A1 Feb. 10, 2022

Related U.S. Application Data

(63) Continuation of application No. PCT/CN2019/122122, filed on Nov. 29, 2019.

(30) Foreign Application Priority Data

Feb. 23, 2019 (CN) .......................... 201910134487.5

(51) Int. Cl.
*A61B 8/00* (2006.01)
*A61B 8/08* (2006.01)

(52) U.S. Cl.
CPC .......... *A61B 8/0866* (2013.01); *A61B 8/4254* (2013.01); *A61B 8/4455* (2013.01);
(Continued)

(58) Field of Classification Search
CPC ... A61B 8/0866; A61B 8/4254; A61B 8/4455; A61B 8/4472; A61B 8/4488; A61B 8/5223; A61B 8/4494; G01S 15/8915
See application file for complete search history.

(56) References Cited

U.S. PATENT DOCUMENTS

2010/0030231 A1* 2/2010 Revie ..................... A61B 90/36
382/128
2013/0102903 A1 4/2013 Tanaka et al.
(Continued)

FOREIGN PATENT DOCUMENTS

CN 101049245 10/2007
CN 101669831 A 3/2010
(Continued)

OTHER PUBLICATIONS

Dinh et al. "Ultrasound Machine Basics-Knobology, Probes, and Modes" (Year: 2020).*
(Continued)

*Primary Examiner* — Alexei Bykhovski
(74) *Attorney, Agent, or Firm* — Burris Law, PLLC

(57) ABSTRACT

A fetal head direction measuring device includes a medical ultrasonic probe for scanning and acquiring a preset ultrasonic image, an angle sensor fixed to the medical ultrasonic probe for sensing an angular change of a scanning direction of the medical ultrasonic probe, and a data processing unit for calculating a fetal head direction. A fetal head direction measuring method includes: obtaining an angle value sensed by the angle sensor at an initial position; acquiring a preset ultrasonic image and recording an angle value sensed by an angle sensor at this time; marking preset fetal head feature points and calculating a directional angle of the preset fetal head feature points in the preset ultrasonic image; and determining the fetal head direction. A fetal head orientation can be measured and calculated more conveniently and flexibly, and the user operation is simpler and more flexible.

7 Claims, 3 Drawing Sheets

(52) U.S. Cl.
CPC .......... *A61B 8/4472* (2013.01); *A61B 8/4488* (2013.01); *A61B 8/5223* (2013.01)

(56) References Cited

U.S. PATENT DOCUMENTS

| | | | | |
|---|---|---|---|---|
| 2013/0237824 | A1* | 9/2013 | Kim | A61B 8/466 |
| | | | | 600/443 |
| 2016/0095581 | A1* | 4/2016 | Yoneyama | A61B 8/4254 |
| | | | | 600/440 |
| 2016/0327520 | A1 | 11/2016 | Ten Grotenhuis et al. | |
| 2019/0038182 | A1* | 2/2019 | Kim | G16H 50/30 |
| 2021/0321937 | A1* | 10/2021 | Amit | A61B 5/6823 |

FOREIGN PATENT DOCUMENTS

| | | | |
|---|---|---|---|
| CN | 102415905 | | 4/2012 |
| CN | 103068316 | | 4/2013 |
| CN | 101669831 B | | 9/2013 |
| CN | 106461618 | | 2/2017 |
| CN | 106963378 | | 7/2017 |
| CN | 107928705 | | 4/2018 |
| CN | 109717906 | | 5/2019 |
| EP | 3155970 | * | 4/2017 |
| JP | 2015171476 | | 10/2015 |
| WO | 2017153301 | | 9/2017 |

OTHER PUBLICATIONS

Nizard, et al. (Determination of Fetal Head Station and Position During Labor: A New Technique That Combines Ultrasound and a Position-Tracking System, American Journal of Obstetrics & Gynecology, Apr. 2009, pp. 404.e1-404.e5. (Year: 2009).*
International Search Report and Written Opinion for International Application PCT/CN2019/122122, mailed Feb. 25, 2020.
Office Action issued in corresponding CN Application No. 201910134487.5, issued Feb. 27, 2020.
Laborpro, Initial Exploration of Clinical Value of Computerized LaborPro System in Pelvimetry and Labour Monitoring, China Academic Journal Electronic Publishing House, Mar. 20, 2015, 89 pages.
Supplementary European Search Report issued in corresponding EP Application 19915723, dated Oct. 12, 2022, 2 pages.
Written Opinion issued in corresponding EP Application 19915723.1, 6 pages.
Nizard, et al., Determination of Fetal Head Station and Position During Labor: A New Technique That Combines Ultrasound and a Position-Tracking System, American Journal of Obstetrics & Gynecology, Apr. 2009, pp. 404.e1-404.e5.
Ghi, et al., Diagnosis of Station and Rotation of the Fetal Head in the Second Stage of Labor With Intrapartum Translabial Ultrasound, Ultrasound Obstet Gynecol 2009, pp. 331-336, vol. 33, John Wiley & Sons, Ltd.
Supplementary search report of corresponding CN priority application (CN202010788850.8) Jul. 27, 2022, 1 page.

* cited by examiner

FETAL HEAD DIRECTION MEASURING DEVICE AND METHOD

CROSS-REFERENCE TO RELATED APPLICATIONS

This application is a continuation application of PCT Patent Application Serial No. PCT/CN2019/122122, filed on Nov. 29, 2019, and claims priority to and benefit of Chinese Patent Application No. 201910134487.5, filed on Feb. 23, 2019 in the China National Intellectual Property Administration, which are incorporated herein by reference in their entireties.

FIELD

The present disclosure relates to the field of obstetric monitoring, and particularly, relates to a fetal head direction measuring device and method.

BACKGROUND

In obstetrics, a dynamic spatial relationship between a fetal head and a pelvis (referred to as the "cephalopelvic relationship") is essential to the selection of delivery methods and handling of delivery. Clinically, these data need to be accurately monitored at any time, aiding scientific decision-making on delivery for doctors and midwives.

In obstetrics, a fetal head direction is one of the important parameters indicating the spatial relationship between the fetal head and the pelvis. The fetal head direction indicates a relationship between a fetal presenting occipital bone and an anterior, posterior, left, or right part of a maternal pelvis, and can be divided into eight orientations: occipito anterior, left occipito anterior, left occipito transverse, left occipito posterior, occipito posterior, right occipito posterior, right occipito transverse, and right occipito anterior. If an abnormal presentation is not corrected, it may cause dystocia during delivery.

A Chinese invention patent No. 201710122274.1, entitled "Electromagnetic Positioning and Ultrasonic Imaging-Based Fetal Head Orientation Measuring Method", provides an electromagnetic positioning and ultrasonic imaging-based fetal head orientation measuring method. According to the method, firstly, coordinates of superior and inferior borders of the pubic symphysis and coordinates of the spinous process of the fifth lumbar vertebra of puerpera are measured by an electromagnetic positioning system; a normal vector of the sagittal plane is calculated; the abdominal cavity of the puerpera is scanned transversely by an integrated probe to obtain an ultrasonic image of fetal head anatomical feature points, and thus a measurement mode is determined; a direction vector of each measurement mode is calculated; an included angle between each direction vector and the normal vector of the sagittal plane is calculated; and finally, a fetal head orientation is confirmed according to the included angle. According to the method, the fetal head feature points are positioned by the ultrasonic and magnetic positioning system, and the fetal head orientation is measured by calculating the included angle between each direction vector and the normal vector of the sagittal plane. The method can conveniently measure a fetal head orientation without digital vaginal examination. However, measuring the fetal head orientation with the above-mentioned method is complicated for the user to operate, and thus the promotion is limited.

SUMMARY

The present disclosure is directed to provide a more convenient and flexible device and method for measuring fetal head orientation to solve the above problems.

To achieve the above objective, the present disclosure provides a fetal head direction measuring device, including a medical ultrasonic probe, an angle sensor, and a data processing unit, wherein the medical ultrasonic probe and the angle sensor are communicably connected with the data processing unit;

the angle sensor is fixed to the medical ultrasonic probe for sensing an angular change of a scanning direction of the medical ultrasonic probe;

the medical ultrasonic probe is configured to scan and acquire a preset ultrasonic image; and the data processing unit is configured to calculate a fetal head direction.

DETAILED DESCRIPTION

The present disclosure will be further described in detail below in conjunction with the embodiments and the drawings, but implementations of the present disclosure are not limited thereto.

EMBODIMENTS

In the present embodiment, a fetal head direction measuring device is provided, including a medical ultrasonic probe, an angle sensor, and a data processing unit, wherein the medical ultrasonic probe and the angle sensor are communicably connected with the data processing unit;

the angle sensor is fixed to the medical ultrasonic probe for sensing an angular change of a scanning direction of the medical ultrasonic probe;

the medical ultrasonic probe is configured to scan and acquire a preset ultrasonic image; and the data processing unit is configured to calculate a fetal head direction.

A Chinese invention patent No. 201710122274.1, published on Jul. 21, 2017, and entitled "Electromagnetic Positioning and Ultrasonic Imaging-Based Fetal Head Orientation Measuring Method", provides an electromagnetic positioning and ultrasonic imaging-based fetal head orientation measuring method. According to the method, an electromagnetic positioning device is used to track a posture of an ultrasonic probe to measure a fetal head orientation.

Six degrees of freedom of the ultrasonic probe can be obtained by the electromagnetic positioning device, and thus the position and posture of the ultrasonic probe in an electromagnetic space can be obtained accurately. According to the device, an electromagnetic positioning sensor needs to be fixed to the ultrasonic probe. However, the cost of an electromagnetic positioning module and a magnetic induction sensor is high, the system is complicated, and thus the structural design of the whole product is limited. Therefore, the applicant proposes a simpler and more convenient technical solution.

Before describing the technical solution of the present embodiment, the following concepts and functions in the present embodiment are described as follows.

Medical ultrasonic probe: a necessary component of ultrasonic diagnostic equipment commonly used in clinical practice, being configured to transmit and receive ultrasonic waves during ultrasonic detection, including linear array type, convex array type, and electronic phased array type. In the present embodiment, the medical ultrasonic probe is a linear array type or convex array type probe. From the appearance point of view, the difference between the linear array type and the convex array type medical ultrasonic probes is that an acoustic lens surface (i.e., a face in contact with a body surface during scanning) of the linear array type medical ultrasonic probe is flat, but the acoustic lens surface of the convex array type medical ultrasonic probe is curved. Preferably, the medical ultrasonic probe is a convex array type probe and configured to scan the abdomen of a puerpera to obtain fetal head anatomical feature points.

Figure 1A:
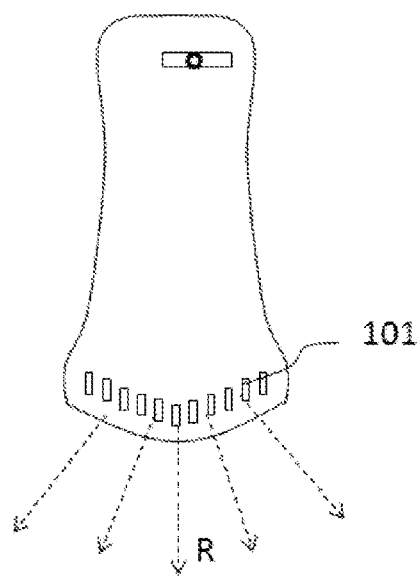
FIG. 1(a) schematically shows a scanning plane and direction of a physical structure of a medical ultrasonic probe.
Figure 1B:
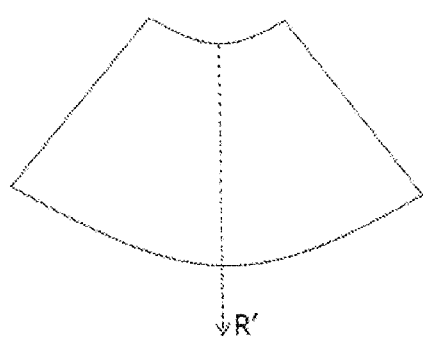
FIG. 1(b) schematically shows a scanning plane and direction of an ultrasonic image of the medical ultrasonic probe.

Medical ultrasonic probe scanning plane: referring to FIGS. 1(a) to 1(b), the medical ultrasonic probe is a convex array type probe, with a chip array 101 provided therein. In the present embodiment, referring to FIG. 1(a), for a physical structure of the medical ultrasonic probe, the medical ultrasonic probe scanning plane is a plane where the ultrasonic chip array 101 is located; and for an ultrasonic image, referring to FIG. 1(b), the medical ultrasonic probe scanning plane is a plane where the ultrasonic scan image is located. The plane where the ultrasonic chip array 101 is located may not completely coincide with the plane where the ultrasonic scan image is located.

The scanning direction of the medical ultrasonic probe: referring to FIGS. 1(a) to 1(b), the medical ultrasonic probe scanning direction is a direction facing outwardly from a centerline of the medical ultrasonic probe scanning plane. In the physical structure of the medical ultrasonic probe, referring to FIG. 1(a), the scanning direction is denoted as R; and in the ultrasonic image, referring to FIG. 1(b), the scanning direction is denoted as R'. The scanning direction R for the physical structure of the medical ultrasonic probe may also not completely coincide with the scanning direction R' for the ultrasonic image. That is to say, an absolute scanning plane and direction of the medical ultrasonic probe are difficult to determine. Therefore, the technical solution of the present embodiment does not focus on an absolute value of the scanning direction of the medical ultrasonic probe, but only focuses on an angular change (relative value) of the scanning direction of the medical ultrasonic probe. However, in some application scenarios, it may be assumed that the scanning plane and the scanning direction R for the physical structure of the medical ultrasonic probe coincide with the scanning plane and the scanning direction R' for the ultrasonic image.

Preset fetal head feature points: feature points reflecting the relationship between a fetal occipital bone and an anterior, posterior, left, or right part of a maternal pelvis, wherein a direction of the fetal head feature points may be an "occipital bone-frontal bone" direction of the brain midline, a direction connecting the two orbits, etc. Preset ultrasonic image: it is an ultrasonic image showing the preset fetal head feature points. When used, the ultrasonic probe is moved to find an ultrasonic image showing the preset fetal head feature points, that is, the preset ultrasonic image.

During delivery, the puerpera is usually in a "recumbent position" when monitoring fetal orientation. When scanning the mid-abdomen of the puerpera with the medical ultrasonic probe, the acoustic lens surface of the medical ultrasonic probe is substantially vertically downward, that is, the scanning direction of the medical ultrasonic probe is substantially vertically downward; when the medical ultrasonic probe is used to scan the right or left abdomen of the puerpera, the acoustic lens surface of the medical ultrasonic probe is inclined to the left or the right at a certain angle according to the position of the fetus in the abdomen, which is embodied as an angular change of the scanning direction of the medical ultrasonic probe. That is to say, the angular change sensed by the angle sensor may reflect a change in position of the ultrasonic probe on the abdomen of the puerpera. Upon obtaining the position of the ultrasonic probe on the abdomen of the puerpera, a fetal head direction can be calculated in combination with the position of the fetal head feature points in the ultrasonic image.

The solution has the following advantages: in the present embodiment, the angular change of the scanning direction of the medical ultrasonic probe is used to reflect the position of the ultrasonic probe on the abdomen of the puerpera, and thus the cost of the technical solution of the present embodiment is lower and the product structure is simpler compared with the electromagnetic positioning technology-based fetal head direction measuring technical solution.

Preferably, the angle sensor includes at least one reference axis and senses a rotation angle of the angle sensor body about the reference axis.

Preferably, the angle sensor is any one of a single-axis inclination sensor, a double-axis inclination sensor, a three-axis inclination sensor, a magnetometer, an acceleration sensor, a six-axis sensor, and a nine-axis sensor.

In the present embodiment, the angle sensor includes at least one reference axis and senses a rotation angle of the angle sensor body about the reference axis. At present, such angle sensors include inclination sensors, magnetometers, acceleration sensors, six-axis sensors, nine-axis sensors, etc. The angle sensor generally includes three types: single-axis type, double-axis type, and three-axis type. Wherein the single-axis sensor body is provided with one reference axis: x-axis; the double-axis sensor body is provided with two reference axes: x-axis and y-axis; the three-axis sensor body is provided with three reference axes: x-axis, y-axis, and z-axis. The x-axis, y-axis, and z-axis all take the angle sensor body as a reference body and sensed data are rotation angles of the angle sensor body about the x-axis, y-axis, and z-axis, respectively. A magnetometer, also known as an electronic compass, senses a rotation angle of the electronic compass body about a vertical axis, taking the geomagnetic north pole as reference zero.

In addition, there are well-established angle sensors on the market, such as acceleration sensors, and three-axis, six-axis, and nine-axis sensors. The acceleration sensor is similar to an inclination sensor. The three-axis sensor is generally a three-axis acceleration sensor, resembling the three-axis inclination sensor described in the present embodiment. The six-axis sensor is generally a three-axis gyroscope+a three-axis accelerometer. The nine-axis sensor generally refers to a three-axis gyroscope+a three-axis accelerometer+a three-axis magnetometer, or a six-axis accelerometer+a three-axis gyroscope, or a six-axis gyroscope+a three-axis accelerometer. According to well-established MEMS (Micro-Electro-Mechanical System) sensors on the market, several gyroscopes, accelerometers and magnetometers are packaged into a single chip, and thus data can be self-complemented, more useful parameters can be measured, which certainly include angle data required in the present embodiment. Therefore, the angle sensors described in the present embodiment include these MEMS sensors that can provide the angle data described in the present embodiment, and these MEMS sensors shall fall within the scope of protection of the present disclosure.

Preferably, the medical ultrasonic probe is a linear array type or convex array type probe, and the plane of the chip array of the medical ultrasonic probe is perpendicular to any reference axis of the angle sensor.

Figure 2:
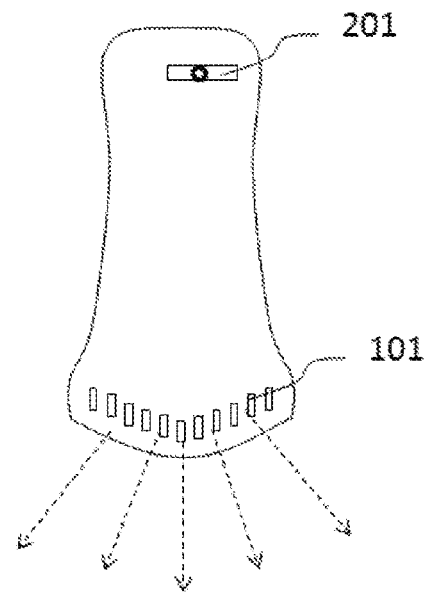
FIG. 2 schematically shows a side cross-sectional view of a chip array of the medical ultrasonic probe and an angle sensor.

As a preferred embodiment, the medical ultrasonic probe is a linear array type or convex array type probe, and the plane of the chip array 101 of the medical ultrasonic probe is perpendicular to any reference axis of the angle sensor 201, as shown in FIG. 2. FIG. 2 schematically shows the plane where the chip array of the medical ultrasonic probe is located and a side view of the angle sensor, and the reference axis of the angle sensor 201 is perpendicular to the plane of the drawing. When the medical ultrasonic probe swings left and right along the plane of the drawing, the angle sensor 201 rotates about the reference axis and senses a leftward or rightward swing angle of the medical ultrasonic probe in real-time.

As described above, the plane where the ultrasonic chip array 101 is located may not completely coincide with the plane where the ultrasonic scan image is located. Therefore, making the plane of the chip array of the medical ultrasonic probe perpendicular to any reference axis of the angle sensor does not improve the measurement accuracy of the angle in the scanning direction of the medical ultrasonic probe. However, within a certain error range, it is considered that the plane where the ultrasonic chip array 101 is located coincides with the plane where the ultrasonic scan image is located, and thus designing the plane where the chip array 101 of the medical ultrasonic probe is located to be perpendicular to any reference axis of the angle sensor 201 brings certain convenience to a method for determining fetal head direction.

A fixed position of the angle sensor and the medical ultrasonic probe will be further described. The plane where the ultrasonic chip array 101 is located may not coincide with the plane where the ultrasonic scan image is located. That is to say, the absolute scanning direction of the medical ultrasonic probe is difficult to determine. Therefore, the technical solution of the present embodiment does not focus on the scanning direction (absolute value) of the medical ultrasonic probe, but only focuses on the angular change (relative value) of the scanning direction of the medical ultrasonic probe. Therefore, in a specific implementation, only a relative position relationship between the angle sensor and the medical ultrasonic probe needs to keep unchanged, and thus an angular change sensed by the angle sensor can reflect the angular change of the scanning direction of the medical ultrasonic probe. In another aspect, within a certain error range, assuming that the plane where the ultrasonic chip array 101 is located coincides with the plane where the ultrasonic scan image is located, which brings certain convenience to the method for determining fetal head direction.

As a preferred embodiment, furthermore, the angle sensor is built in the medical ultrasonic probe.

As a preferred embodiment, furthermore, the medical ultrasonic probe is a wireless ultrasonic probe, and the medical ultrasonic probe and the angle sensor are communicably connected with the data processing unit wirelessly.

As a preferred embodiment, furthermore, the angle sensor is built in the medical ultrasonic probe. The medical ultrasonic probe is a wireless ultrasonic probe, and the medical ultrasonic probe and the angle sensor are communicably connected with the data processing unit wirelessly. The design has the following advantages: the user operation is not restricted by cables, and thus the operation is more convenient and the user experience is better. Furthermore, in the present embodiment, a fetal head direction measuring method using the fetal head direction measuring device is provided, including the following steps: acquiring a preset ultrasonic image, and recording an angle value sensed by an angle sensor at this time; marking preset fetal head feature points, and calculating a directional angle of the preset fetal head feature points in the preset ultrasonic image; and determining the fetal head direction.

Figure 3:
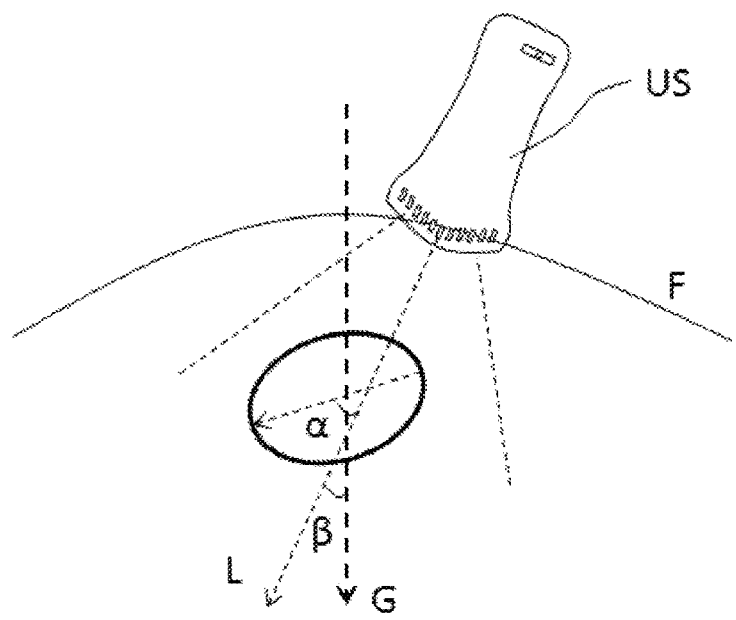
FIG. 3 schematically shows the principle of the method for measuring fetal head direction.

Referring to FIG. 3, in the present embodiment, the medical ultrasonic probe is a linear array type or convex array type probe, and the plane of the chip array of the medical ultrasonic probe is perpendicular to any reference axis of the angle sensor. It is assumed that the plane where the ultrasonic chip array 101 is located coincides with a plane where the ultrasonic scan image is located and the angle value sensed by the angle sensor in the vertical direction is 0 degrees. When the puerpera is in a "recumbent position", the abdominal surface of the puerpera is denoted as an arc line F, the vertical direction (that is, the direction of gravity) is denoted as G and represents a "pubic symphysis→sacrum" direction of the puerpera, the angle value sensed by the angle sensor is denoted as β, and the angle value β represents an included angle between the scanning direction L of the medical ultrasonic probe US and the vertical direction G. The directional angle of the preset fetal head feature points in the preset ultrasonic image is denoted as α, that is, an included angle between a connecting line of the preset fetal head feature points and the scanning direction L of the medical ultrasonic probe US is α. The preset fetal head feature points refer to fetal head feature points that can represent the fetal head direction, such as fetal brain midline (occipital bone→frontal bone). In conjunction with the definition of the fetal head direction (relationship between a fetal presenting occipital bone and an anterior, posterior, left or right part of a maternal pelvis: occipito anterior, left occipito anterior, left occipito transverse, left occipito posterior, occipito posterior, right occipito posterior, right occipito transverse, and right occipito anterior), an included angle (α+β) between the connecting line of the preset fetal head feature points (occipital bone→frontal bone) and the vertical direction G (symphysis pubis→sacrum) can be used to determine the fetal head direction. The method provided in the present embodiment can be implemented by a single-axis sensor, such as a single-axis inclination sensor, a magnetometer, etc.

Although, in practice, the plane where the ultrasonic chip array 101 is located does not coincide with the plane where the ultrasonic scan image is located, and the angle value sensed by the angle sensor in the vertical direction is not necessarily 0 degree, and thus a calculated angle change may have a certain error. However, such an error is acceptable during measuring the fetal head direction.

Furthermore, in the present embodiment, an improved fetal head direction measuring method is provided, including the following steps:

obtaining an angle value sensed by the angle sensor at an initial position;

acquiring a preset ultrasonic image, and recording an angle value sensed by an angle sensor at this time;

marking preset fetal head feature points, and calculating a directional angle of the preset fetal head feature points in the preset ultrasonic image; and determining the fetal head direction.

Furthermore, as a preferred embodiment, the step of obtaining an angle value sensed by the angle sensor at an initial position includes:

placing the medical ultrasonic probe in a vertically downward direction, and obtaining the angle value sensed by the angle sensor at this time.

In the present embodiment, the initial position refers to an angle value sensed by the angle sensor when scanning along preset pelvic feature points of the puerpera with the ultrasonic probe. By measuring the angle at the initial position, first, a pelvic orientation of the puerpera can be determined, then an angular change at a measurement position is a deflection angle of the ultrasonic probe. During an obstetric examination, the puerpera is in a "recumbent position". Therefore, the vertically downward scanning of the medical ultrasonic probe can represent the "pubic symphysis→sacrum" direction of the puerpera. In a specific implementation, to obtain the angle value sensed by the angle sensor at the initial position more accurately, the medical ultrasonic probe should be placed closer to the vertically downward direction, and in this case, some tools such as a level gauge may be used.

The step of obtaining the angle value sensed by the angle sensor at the initial position is added, factors like the plane where the ultrasonic chip array 101 is located coinciding with the plane where the ultrasonic scan image is located or not, and the angle value sensed by the angle sensor in the vertical direction being not necessarily 0 degree are excluded, and at the same time, the plane of the chip array of the medical ultrasonic probe may not be perpendicular to any reference axis of the angle sensor, which reduces the difficulty of fixing the angle sensor to the medical ultrasonic probe in implementations.

However, this would increase the number of measuring steps are increased and cause some trouble to the users.

Furthermore, as a preferred embodiment, the step of determining the fetal head direction includes the following steps:

calculating an ultrasonic scanning direction vector I0 at the initial position according to the angle value sensed by the angle sensor at the initial position;

calculating an ultrasonic scanning direction vector I1 at a measurement position according to the angle value sensed by the angle sensor when acquiring the preset ultrasonic image;

calculating an included angle δ between the vectors I0 and I1; and determining the fetal head direction according to the directional angle of the preset fetal head feature points in the preset ultrasonic image and the included angle δ.

Figure 4A:
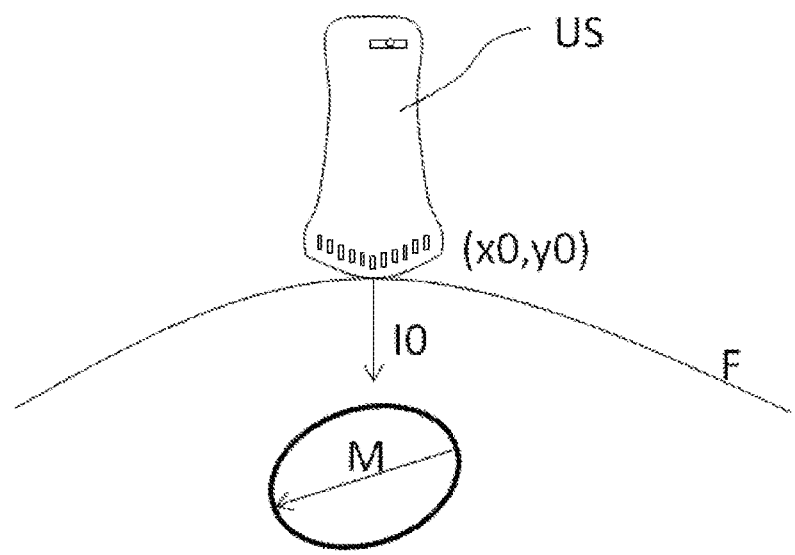
FIG. 4(a) schematically shows the principle of an improved method for measuring fetal head direction.
Figure 4B:
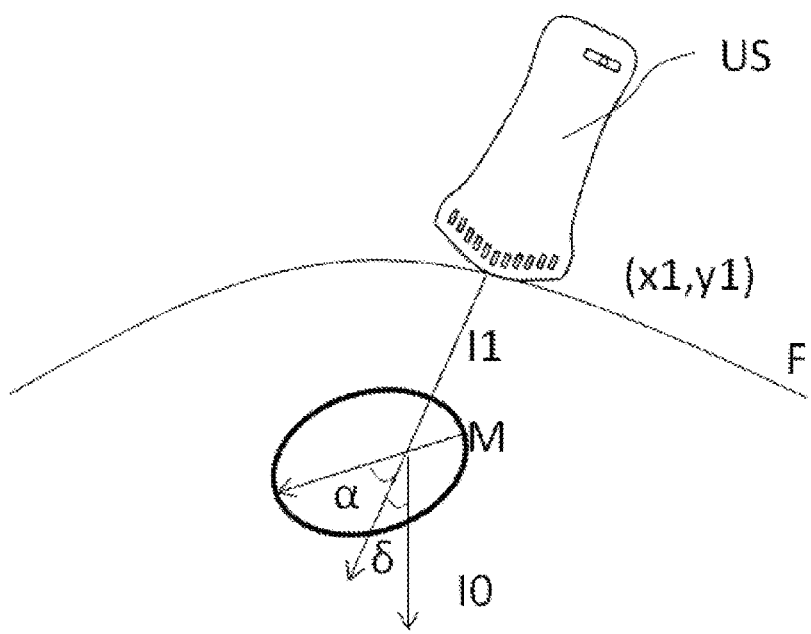
FIG. 4(b) schematically shows the principle of an improved method for measuring fetal head direction in addition.

Taking the double-axis angle sensor as an example, referring to FIG. 4(*a*) and FIG. 4(*b*), it is assumed that the angle value sensed by the angle sensor includes rotation angles about the x-axis and the y-axis. At the initial position, an angle value sensed by the angle sensor is (x0, y0), that is, at the initial position, the angle sensor respectively rotates x0 degrees about the x-axis and y0 degrees about the y-axis from a zero vector (0, 0, 1), and then an ultrasonic scanning direction vector I0 at the initial position is (cosx0(−siny0), sinx0, cosx0cosy0), which also represents a certain orientation of the maternal pelvis. Preferably, the initial vector I0 represents the "pubic symphysis→sacrum" direction of the puerpera. When acquiring the preset ultrasonic image, the angle value sensed by the angle sensor is (x1, y1), that is, at a measurement position, the angle sensor respectively rotates x1 degrees about the x-axis and y1 degrees about the y-axis from the zero vector (0, 0, 1), the ultrasonic scanning direction vector I1 of the measurement position is (cosx1(−siny1), sinx1, cosx1cosy1), and thus the angle for vector I0→I1, that is, an angular change δ of the angle sensor, can be calculated. Then, according to the directional angle α of the preset fetal head feature points in the preset ultrasonic image and the angular change δ of the angle sensor, an angle between the connecting line (occipital bone→frontal bone) of the preset fetal head feature points and the initial vector I0, that is, an included angle (α+β) between the connecting line (occipital bone→frontal bone) of the preset fetal head feature points and the puerpera (symphysis pubis→sacrum), is calculated to determine the fetal head direction.

Similarly, taking the three-axis angle sensor as an example, it is assumed that the angle value sensed by the angle sensor includes rotation angles about the x-axis, y-axis, and z-axis. At the initial position, the angle value sensed by the angle sensor is (x0, y0, z0), that is, at the initial position, the angle sensor respectively rotates x0 degrees about the x-axis, y0 degrees about the y-axis, and z0 degrees about the z-axis from a zero vector, and then an ultrasonic scanning direction vector I0 of the initial position can be calculated, which also represents a certain orientation of the maternal pelvis. Preferably, the initial vector I0 represents the "pubic symphysis→sacrum" direction of the puerpera. When a preset ultrasonic image is acquired, the angle value sensed by the angle sensor is (x1, y1, z1), that is, at a measurement position, the angle sensor respectively rotates at x1 degrees about the x-axis, at y1 degrees about the y-axis and z1 degrees about the z-axis from the zero vector, an ultrasonic scanning direction vector I1 of the measurement position can be calculated, and then an angle of vector I0→I1, that is, an angular change δ of the angle sensor, is calculated. Then, according to the directional angle α of the preset fetal head feature point in the preset ultrasonic image and the angular change δ of the angle sensor, an angle between the connecting line (occipital bone→frontal bone) of the preset fetal head feature point and the initial vector I0, that is, an included angle (α+β) between the connecting line (occipital bone→frontal bone) of the preset fetal head feature point and the puerpera (symphysis pubis→sacrum), is calculated to confirm a fetal head direction.

Compared with the prior art, the fetal head direction measuring device and method according to the present disclosure has the following advantages and beneficial effects:

1. According to the fetal head direction measuring device provided in the present disclosure, the angular change of the scanning direction of the medical ultrasonic probe is used to reflect a position of the ultrasonic probe on the abdomen of a puerpera, and thus the cost of the technical solution is lower, and the product structure is simpler.

2. The fetal head direction measuring device provided in the present disclosure can use a wireless ultrasonic probe, and thus users can measure a fetal head orientation more conveniently, and the operation is simpler and more flexible.

3. According to the fetal head direction measuring method provided in the present disclosure, the angular change of the scanning direction of the medical ultrasonic probe is used to reflect a position of the ultrasonic probe on the abdomen of a puerpera, and thus the cost of the technical solution is lower, the product structure is simpler, and the operation is more convenient.

The above embodiments are preferred implementations of the present disclosure, but the implementations of the present disclosure are not limited thereto. Any other variation, modification, substitution, combination, and simplification that made without departing from the spirit and principle of the present disclosure shall be regarded as equivalent replacement and fall within the scope of the present disclosure.

What is claimed is:

1. A fetal head direction measuring device, comprising a medical ultrasonic probe, an angle sensor, and a data processing unit, wherein the medical ultrasonic probe and the angle sensor are communicably connected with the data processing unit;
the angle sensor is fixed to the medical ultrasonic probe for sensing an angular change of a scanning direction of the medical ultrasonic probe without sensing location of the angle sensor;
the medical ultrasonic probe is configured to scan and acquire a preset ultrasonic image and to scan and acquire an ultrasonic image at an initial position; and
the data processing unit is configured to calculate a fetal head direction according to a directional angle α of preset fetal head feature points in the preset ultrasonic image and an included angle δ between an ultrasonic scanning direction vector I0 at an initial position of the probe according to an angle value sensed by the angle sensor at the initial position and an ultrasonic scanning direction vector I1 at a measurement position according to the angle value sensed by the angle sensor when acquiring the preset ultrasonic image and further wherein in the ultrasonic image acquired at said initial position the data processing unit is configured to determine a maternal pelvis orientation.

2. The fetal head direction measuring device of claim 1, wherein the angle sensor comprises at least one reference axis and senses a rotation angle of the angle sensor body about the reference axis.

3. The fetal head direction measuring device of claim 2, wherein the angle sensor is any one of a single-axis inclination sensor, a double-axis inclination sensor, a three-axis inclination sensor, a magnetometer, an acceleration sensor, a six-axis sensor, and a nine-axis sensor.

4. The fetal head direction measuring device of claim 2, wherein the medical ultrasonic probe is a linear array type or convex array type probe, and a plane of a chip array of the medical ultrasonic probe is perpendicular to any one of the at least one reference axis of the angle sensor.

5. The fetal head direction measuring device of claim 4, wherein the angle sensor is built in the medical ultrasonic probe.

6. The fetal head direction measuring device of claim 5, wherein the medical ultrasonic probe is a wireless ultrasonic probe, and the medical ultrasonic probe and the angle sensor are communicably connected with the data processing unit wirelessly.

7. A fetal head direction measuring method based on the fetal head direction measuring device of claim 1, the method comprising the following steps:
obtaining an angle value sensed by the angle sensor at an initial position of the probe;
acquiring an ultrasonic image at said initial position;
determining, in the ultrasonic image acquired at said initial position, a maternal pelvis orientation;
calculating an ultrasonic scanning direction vector I0 at the initial position according to the angle value sensed by the angle sensor at the initial position;
acquiring a preset ultrasonic image, and recording the angle value sensed by the angle sensor;
calculating an ultrasonic scanning direction vector I1 at a measurement position according to the angle value sensed by the angle sensor when acquiring the preset ultrasonic image;
marking preset fetal head feature points in the preset ultrasonic image, and calculating a directional angle α of the preset fetal head feature points in the preset ultrasonic image;
calculating an included angle δ between the vectors I0 and I1; and
determining the fetal head direction according to the directional angle α of the preset fetal head feature points in the preset ultrasonic image and the included angle δ.

* * * * *